United States Patent [19]

Glace

[11] Patent Number: 5,158,092
[45] Date of Patent: Oct. 27, 1992

[54] METHOD AND AZIMUTHAL PROBE FOR LOCALIZING THE EMERGENCE POINT OF VENTRICULAR TACHYCARDIAS

[76] Inventor: Christian Glace, 12, rue du Vivarais, F-54500, Vandoeuvre, France

[21] Appl. No.: 382,787
[22] PCT Filed: Oct. 27, 1988
[86] PCT No.: PCT/FR88/00525
§ 371 Date: Aug. 28, 1989
§ 102(e) Date: Aug. 28, 1989
[87] PCT Pub. No.: WO89/03657
PCT Pub. Date: May 5, 1989

[30] Foreign Application Priority Data

Oct. 27, 1987 [FR] France ............................... 87 15027

[51] Int. Cl.$^5$ ............................................. A61B 5/04
[52] U.S. Cl. ........................................ 128/705; 128/642; 128/696
[58] Field of Search ............... 128/705, 702, 699, 696, 128/419 P, 642

[56] References Cited

U.S. PATENT DOCUMENTS

| | | | |
|---|---|---|---|
| 4,628,937 | 12/1986 | Hess et al. | 128/798 |
| 4,649,924 | 3/1987 | Taccardi | 128/419 P |
| 4,660,571 | 4/1987 | Hess et al. | 128/784 |
| 4,690,148 | 9/1987 | Hess | 128/798 |
| 4,699,147 | 10/1987 | Chilson et al. | 128/642 |

OTHER PUBLICATIONS de Bakker et al., "Endo. Card. Mapping by Simul. Recording of Endo, ECG's During Card. Surgery", Journal of the Amer. Col. of Card., vol. 2, #5, Nov. 1983.
Savard et al., "Interactive Electrophys Mapping Sys.", IEEE 1985 Compint Computer Aided Technologies, Montreal, Quebec, Canada, 9-13, Sep. 1985, pp.76-78.

Primary Examiner—William E. Kamm
Assistant Examiner—Kennedy J. Schaetzle
Attorney, Agent, or Firm—Weiser & Stapler

[57] ABSTRACT

Device permitting localization of the emergence point of ventricular tachycardias in cardiological medicine, characterized, in comparison with traditional cardiac mapping, by: a precision of the same order, its speed of use, its low cost and the further possibility of localizing the macro-re-entry pathway (around aneurysms, for example).

In distinction to traditional mapping, this device dispenses with the construction of a map of isochrones (14).

The principle of the device according to the invention is based on localization of the propagation of the myocardial cell depolarization, or of the muscle contraction of the heart (15) which results directly therefrom. This localization is carried out in stages (17) over the length of its pathway (13) from an arbitrary point (16) on the heart chosen by the operator, retracing this pathway as far as its source (12'), which is referred to as the emergence point.

35 Claims, 4 Drawing Sheets

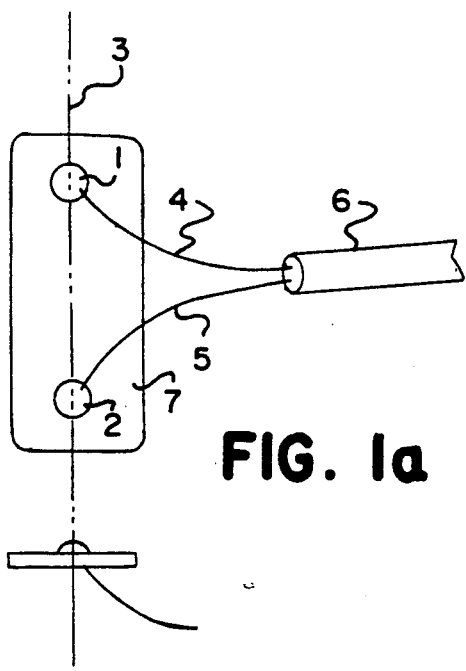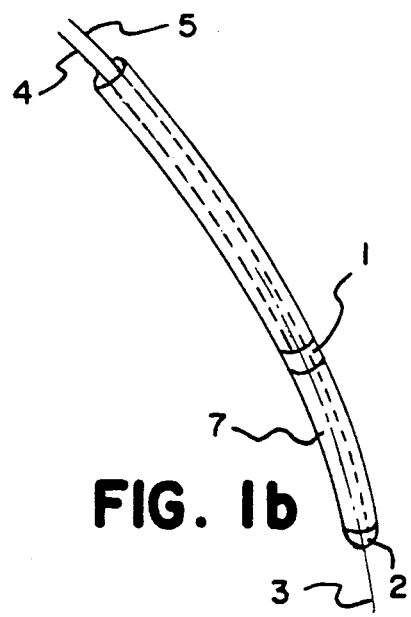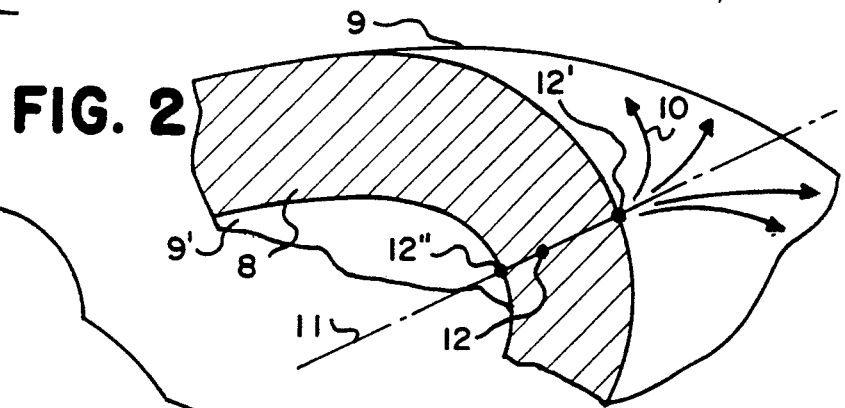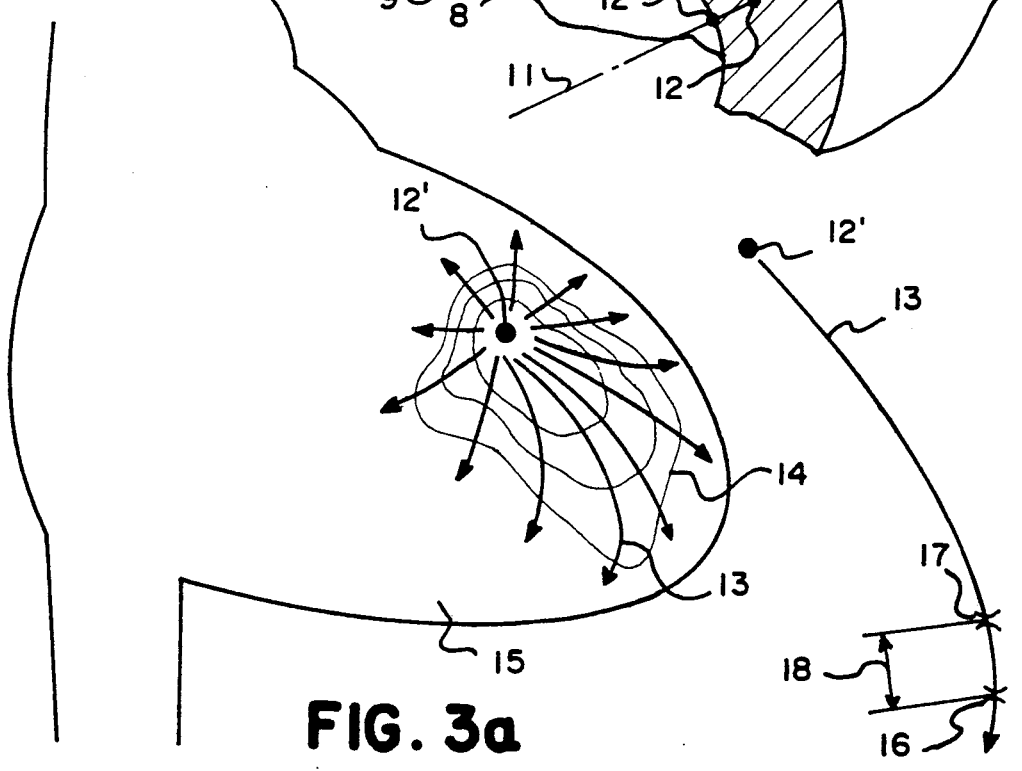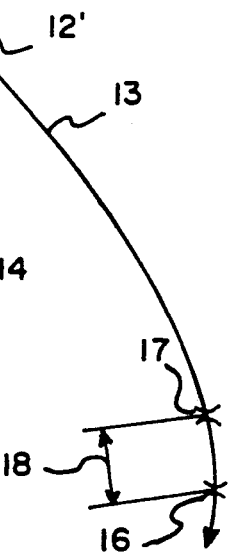

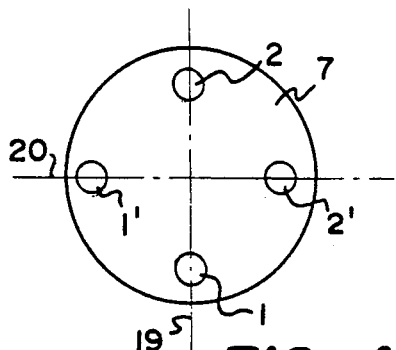
FIG. 4a
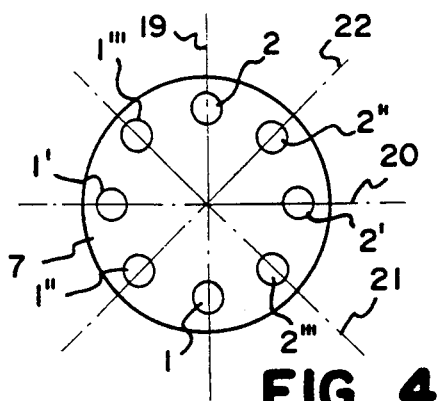
FIG. 4b
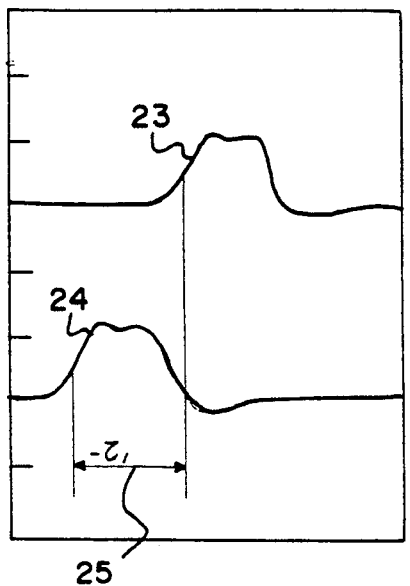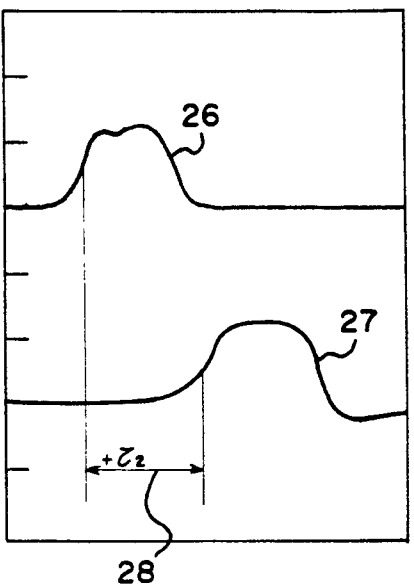
FIG. 5
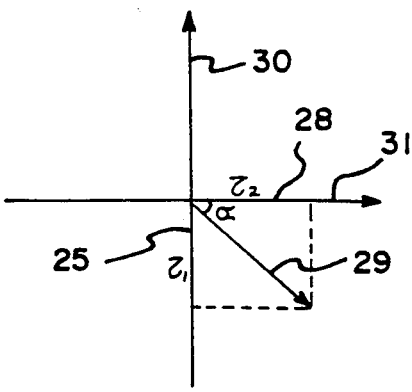
FIG. 6
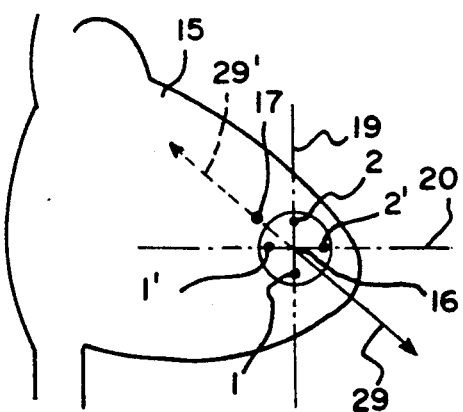
FIG. 7

METHOD AND AZIMUTHAL PROBE FOR LOCALIZING THE EMERGENCE POINT OF VENTRICULAR TACHYCARDIAS

The present invention relates to a device permitting localization of the emergence point of ventricular tachycardias in cardiological medicine, by a successive approach method, characterized, in comparison with traditional cardiac mapping, by: a precision of the same order, its speed of use, its low cost and the further possibility of localizing the macro-re-entry pathway (around aneurysms, for example).

In distinction to traditional mapping, this device dispenses with the construction of a map of isochrones.

The techniques currently used are either manual or automatic, and are applied to the epicardium, the endocardium or the myocardium itself: A) Epicardium/Manual method: a three-pole probe is moved on the surface of the heart, while a reference electrode is attached close to the base of the aorta.

An electrocardiograph comprising:
a trace for the surface ECG,
two traces for the reference electrocardiogram and that of the mobile probe,
enables the horizontal distance on the paper between the deflections to be measured at the time which has elapsed (interval) between the depolarizations perceived by the reference electrode and the mobile electrode.

Several interval values enable a map of isochrones (equal interval curves) to be constructed, giving a two-dimensional view of the propagation of the depolarization. The point on this map corresponding to the shortest interval is considered to be the emergence point, which is accordingly subjected to surgical removal. This removal may be carried out by ventriculotomy with a scalpel, by diathermy or by a cryosurgical technique.

B) Epicardium/Automatic method: an epicardial net supports from 50 to more than 300 electrodes each connected to an instrumentation amplifier. Each route is multiplexed, sampled/blocked and converted to digital form. A processor acquires these data, processes them and displays them on a monitor or printer in list or image form.

C) Myocardium: a needle equipped with several electrodes provides information about the depth of the emergence point in the thickness of the myocardium.

D) Endocardium/Manual method: a catheter is positioned at different points of the endocardium. The location corresponding to the earliest interval, relative to the reference catheter, is subjected to fulguration.

E) Endocardium/Automatic method: an endocavitary inflatable balloon containing several tens of electrodes permits localization of the emergence point using the acquisition system described in B).

The principle of the device according to the invention is based on localization of the propagation of the myocardial cell depolarization, or of the muscle contraction of the heart which results directly therefrom. This localization is carried out in stages over the entire length of its pathway from an arbitrary point on the heart chosen by the operator, retracing this pathway as far as its source, which is referred to as the emergence point.

The device according to the invention comprises a probe connected to electronic circuits which are designed to process the signals gathered by the probe and to control a device/operator interface. The device according to the invention is referred to as an "azimuthal probe", the two words not being separated in this case.

The term "probe" is reserved for an assembly comprising the sensors, their support, the electrical linking cable with its connector and any means of signalling which are attached thereto and intended for the operator.

The probe is composed of at least one assembly of two sensors sensitive to myocardial depolarization (electrochemical phenomenon) or to cardiac contraction (mechanical phenomenon which is the consequence thereof). Each assembly of two sensors is arranged on an approximately rectilinear axis. The sensors are attached to a support which the operator moves over the epicardium or over the endocardium.

The azimuthal probe enables the following to be determined:
the sense of the propagation of the myocardial cell depolarization or of the cardiac muscle contraction which results directly therefrom, the common source of which is the activation of the emergence point; this sense is determined along the direction represented by the axis of the two sensors, when the operator can note the order of arrival of the activation potentials under one sensor and then under the other (phase shift); if these arrivals are simultaneous, the phase shift is zero;
the direction of this propagation, by several phase shift measurements as above, when the probe is rotated about an axis passing between the two sensors and perpendicular to the cardiac surface; the direction is determined, either when the operator can note the maximum phase shift, the axis of the sensors then being coincident with the direction, or when the operator can note a zero phase shift, the axis of the sensors then being perpendicular to the direction;
the pathway of the depolarization, starting from an arbitrary point on the heart, and carrying out at each stage a determination of sense and direction as described above, followed by a movement of the probe on or in the heart by a distance of the order of one centimeter, to be determined by experience, in the opposite sense and in the direction which have just been determined.

The emergence point is reached after several stages as just described. This point is recognized by the fact that the depolarization is propagated centripetally from it. The phase shifts measured at this point are hence all zero.

With the object of improving the azimuth discrimination during one and the same measurement, the assemblies of two sensors are combined on a single probe according to two or more directions. Each assembly of sensors provides information which is transmitted to the operator. The uncertainty $\epsilon$ about the direction is calculated by:

$$\epsilon = \frac{180}{n}$$

where:
$\epsilon$ is expressed in degrees
n = number of groups of two sensors

To avoid the multiplication of sensors, the device comprises, in an improved version, only two assemblies of two sensors arranged according to two perpendicular axes. Each assembly provides two signals combined in one phase-shift signal. Each phase shift, transferred to an orthonormal reference system, is considered to be the projection of a vector on this reference system. This vector coincides approximately with the azimuth of the depolarization. The vector indicates the sense and direction in which it is necessary to move in order to carry out the next stage of measurement.

Incidentally, the operator can then localize the depth of the seat of activation of the tachycardia by pushing in, in successive stages, a needle comprising an assembly of two sensors, at the location previously determined, namely the emergence point. This point is, in fact, the electrical projection of the seat of activation, on the endocardium or epicardium according to the route first used by the operator. The seat of activation is found when the phase shift between the two signals recorded by the sensors is zero (no preferential senses). There is no need for the direction to be determined by the device, since it is represented by the axis of the needle. In a second step, the operator employs a means of destruction of the region thus localized, the operation of which is authorized by the device and the active portion of which is located on the needle. By way of example, this active portion can be:

a group of electrodes conveying an electric current produced by a high-frequency diathermy generator (electric scalpel) or a cardiac defibrillator, a heat resistor, a duct carrying a refrigerant fluid (cryosurgery).

The device according to the invention comprises electronic circuits designed to process the signal provided by the sensors, to provide signals carrying the desired information (azimuth of the depolarization and location of the emergence point), and optionally to control a destruction device, internal or provided by the user. Each sensor is followed by a processing circuit comprising an amplifier, a filter designed to select the useful component of the signal and hysteresis comparators converting the analogue signals to binary logic signals. This circuit is referred to as a "channel". The channels are grouped in pairs, corresponding to the assemblies of two sensors. Two corresponding channels are connected at their output to a logic phase detector, from which the resulting signal is characteristic of the phase shift between the signals provided by the assembly of two sensors in question. In the case of the vectorial process described above, the two phase shifts derived from the four sensors are combined so as to reconstruct the desired vector.

The device is designed in such a way that the leakage current towards the patient is maintained within statutory limits (for example: exclusive power supply by accumulators, use of isolation amplifiers or optical couplers).

Each amplifier is protected by a limiter from voltage surges which may be produced by equipment used simultaneously by the operator.

When a ventricular tachycardia is not spontaneous, it is necessary to induce it by an impulse generator known as an "external cardiac stimulator", connected to the heart by conductor electrodes. In order for the present device to preserve its capacity to operate, it is necessary to insert an analogue switch in the measuring chain, controlled by the impulses of the stimulator.

All the signals derived from the circuits described are conveyed to an interface means between the device and the operator, employing one of his physiological senses, namely sight, hearing, touch, which indicates to him:

on the one hand, either the sense and direction in which the myocardial depolarization is propagated, or the sense and direction in which the probe must be moved in order to carry out the next stage of acquisition;

on the other hand, where appropriate, the absence of a phase shift in all directions, and hence the localization of the emergence point under the position concurrently occupied by the probe; this result authorizes the use of the means of destruction integrated in the azimuthal probe, or any other external device provided by the user.

The functions carried out by the wired electrical circuits described above are carried out, in another version of the device, by a computer receiving the signals derived from the sensors after amplification, and carrying out similar functions of the device, to the extent that the latter are programmed. This computer is provided with its peripherals for an analogue-to-digital conversion and interface with he user.

FIGS. 1a and 1b show embodiments, given by way of example, of the end of the probe in the basic version of the device according to the invention; in "a" the epicardial probe, in "b" the endocardial catheter.

FIG. 2 shows, in section, the wall of the heart containing the seat of activation and the corresponding emergence points.

FIG. 3 shows, in "a" the propagation of the cardiac depolarization from the emergence point, and in "b" a pathway of the depolarization wave with two stages of measurement carried out with the device.

FIGS. 4a and 4b show embodiments, given by way of example, of the end of the probe in improved versions.

FIG. 5 shows the four signals derived from the vectorial version of the device, grouped in pairs, producing the two phase shift values after processing.

FIG. 6 shows the reconstruction of the depolarization vector using the above two phase shifts.

FIG. 7 shows this vector superposed on the position concurrently occupied by the probe, and the directions and senses in which the operator must move the probe in order to carry out the next stage of acquisition.

FIG. 14b shows the arrangement of the indicator lamps on the probe, the control of which is performed by the circuit of FIG. 14a.

Figure 8:
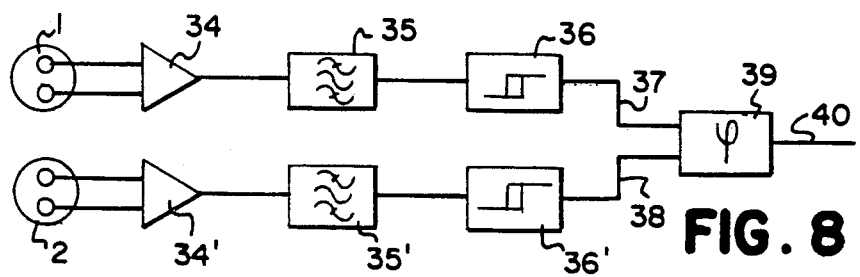
FIG. 8 shows the block diagram of the basic electronic circuits used in the device.

In FIGS. 1a and 1b, the examples of a probe comprise two sensors (1) and (2), arranged on an approximately rectilinear axis (3), attached to a support (7) and equipped with electrical conductors (4) and (5), which are themselves contained in a cable (6) which conveys the signals to be utilized by the electronic circuits of the device.

FIG. 2 shows, in a portion of myocardium (8) in section, the seat of activation (12) of the ventricular tachycardia, and its electrical projections (12') and (12") on the epicardium (9) and on the endocardium (9'), that is to say the emergence points. The line (10) shows an example of a pathway followed by the myocardial depolarization from the seat of activation (12).

FIG. 3a shows a heart (15), comprising an epicardial emergence point (12'), producing centripetal depolarizations (13) which vary in speed in accordance with the local conduction conditions. The curves for equal intervals of depolarization from the point (12') are known as isochrones (14).

FIG. 3b shows a detail of FIG. 3a, locating an arbitrary starting point (16) when the device according to the invention is used, as well as the first stage (17) located at a distance (18) from the starting point. The distance (18) depends on the operator's experience. It will be smaller (a few millimeters) for a beginner. The orientation of the point (17) relative to (16) is determined in accordance with the indications of the device when it is at (16).

The description which follows gives an example of an embodiment of the device according to the invention. The working end of the probe is shown in FIGS. 4a and 4b. Two assemblies of two sensors (1), (2) and (1'), (2') are arranged at right angles according to two axes (19) and (20) on a support (7). The sensors are less than 50 millimeters apart. This distance is inversely proportional to the capacity of the circuits to discriminate the phase shift of the signals, dependent on the bulk tolerated for the probe and proportional to the precision required of the device. Each sensor is, in the present case, composed of two electrodes each connected to an input of the instrumentation amplifier, the input impedance of which is adjustable. The spacing of the electrodes and the impedance must be sufficiently low to separate the local potentials from the remote potentials generated by the myocardium, given that excessively low spacing and impedance values no longer enable signals of sufficient amplitude to be recorded. A probe having an additional two assemblies of two sensors (1"), (2") and (1'''), (2''') arranged according to two additional axes (21) and (22), is shown in FIG. 4b.

A few tests of probes of different sizes enable the best compromise to be found.

The signals (23), (24) and (26), (27) derived, respectively, the sensors (1), (2) and (1'), (2') and shown in FIG. 5 are compared, in pairs, from the standpoint of their phase, resulting in phase shift signals (25) and (28).

In FIG. 6, the algebraic values of these phase shifts are transferred to an orthonormal reference system (30) and (31). These two segments represent the projections, in the plane of the probe support (7), of a vector (29) which can be superposed on the direction and sense of the myocardial depolarization. The trigonometric angle $\alpha$ formed with the positive semi-axis (29) is calculated by:

$$\alpha = \text{Arc tg}\frac{\tau_1}{\tau_2}$$

where: $\tau_1$=delay (23)
$\tau_2$=delay (26)
and: $(\tau_1, \tau_2)\epsilon R^2$ The angle is the so-called "azimuth" of the depolarization at the point where the probe is located.

In FIG. 8, the signals are processed by wired analogue and digital electronic circuits comprising, per sensor (1) or (2):

an amplifier (34) or (34') which brings the signal to a voltage and an impedance compatible with the following circuits, a filter (35) or (35') designed to select the useful portion of the signal, a hysteresis comparator (36) or (36') which converts the signal to a form which can be utilized by logic circuits.

The two resultant outputs (37) and (38) are compared by a phase detector (39) which produces a signal (40) characteristic of the phase shift between the events detected by (1) and (2). The two lines (37) and (38) convey the signals (23) and (24), respectively, of FIG. 5. The line (40) conveys an impulse which corresponds to the delay (25) in FIG. 5. This delay has a value measured in milliseconds, and has an algebraic sign depending on whether (24) is ahead of or behind (23).

The circuit shown in FIG. 8 has to be duplicated in order to process the signals derived from the sensors (1') and (2') of FIG. 4a. This results in two phase shift signals (40) and (40').

Figure 10:
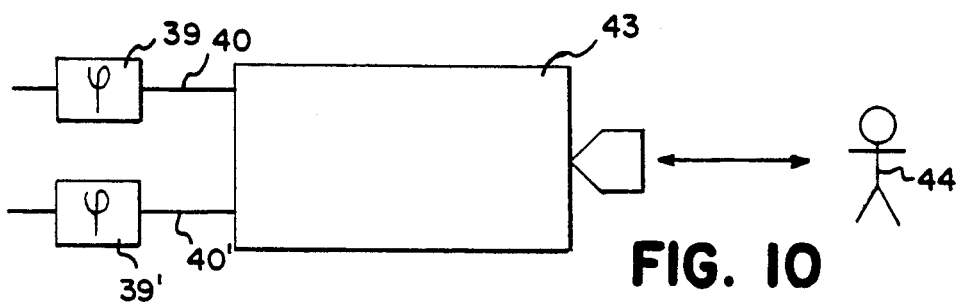
FIG. 10 shows the block diagram of the device/operator interface.

In FIG. 10, the operator (44) is provided with the azimuth indication by an interface means (43) collecting the phase shift signals (40) and (40') derived from the two phase comparators (39) and (39').

Figure 14A:
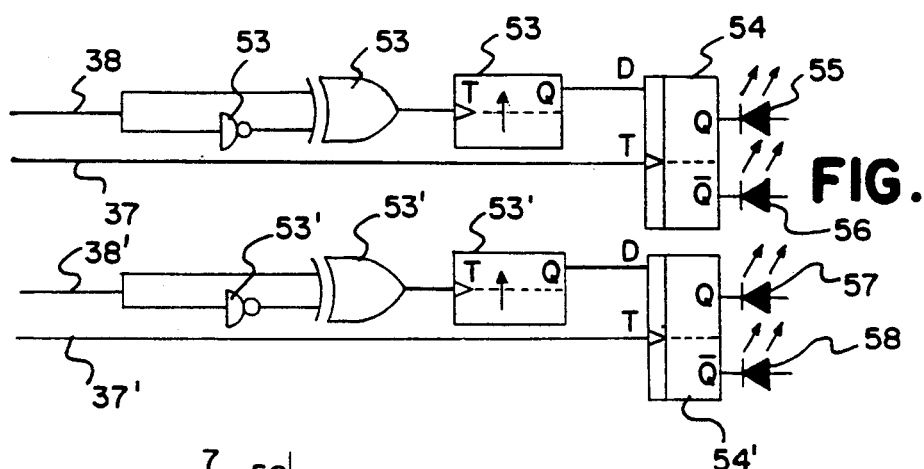
FIG. 14a shows an embodiment, given by way of example, of the device/user interface, preceded by the detector corresponding thereto.
Figure 14B:
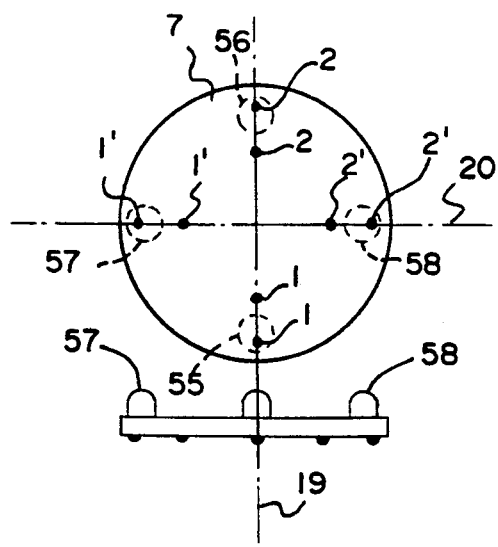

A simple example of embodiment of the interface is given in FIG. 14a. The signals (38), via a monostable (53) set at 50 ms and triggered by the rising and falling fronts, and (37) control a flip-flop D, the complementary outputs Q and $\overline{Q}$ of which adopt a 0 or 1 logic level according to the order of appearance of the signals at the input. Two of the four light-emitting diodes (55), (56), (57) and (58) are illuminated to indicate the azimuth from which the depolarization originates. The operator moves the probe accordingly in this direction and sense in order to perform the next stage of acquisition.

Figure 9:
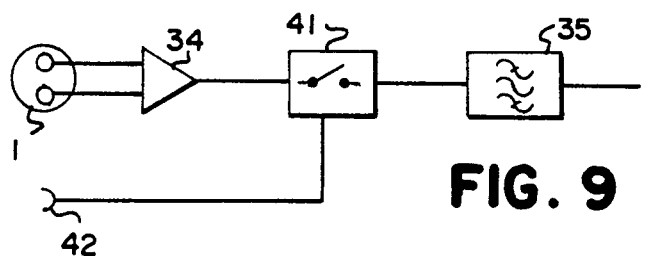
FIG. 9 shows the block diagram of the means of elimination of the impulses originating from the external cardiac stimulator.

In FIG. 9, if it is used, an external cardiac stimulator connected directly to the input (42) is used to control an analogue gate (41) blocking or otherwise the signals originating from the probe. In the absence of an impulse, the switch (41) is closed and allows the signals originating from the sensor (1) to pass through. During the impulse, the switch (41) is open and prevents the signal corresponding to the impulse, which is conducted by the heart, from interfering with the operation of the device.

Figure 12:
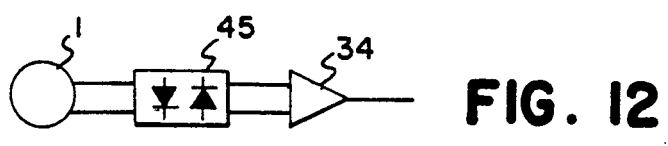
FIG. 12 shows the limiter designed to protect the amplifier from voltage surges.

In FIG. 12, the amplifier (34) is protected at its input, by a limiter (45), against voltage surges which are introduced by devices which the operator may use in proximity to the probe (for example: electric scalpel, defibrillator).

Figure 13:
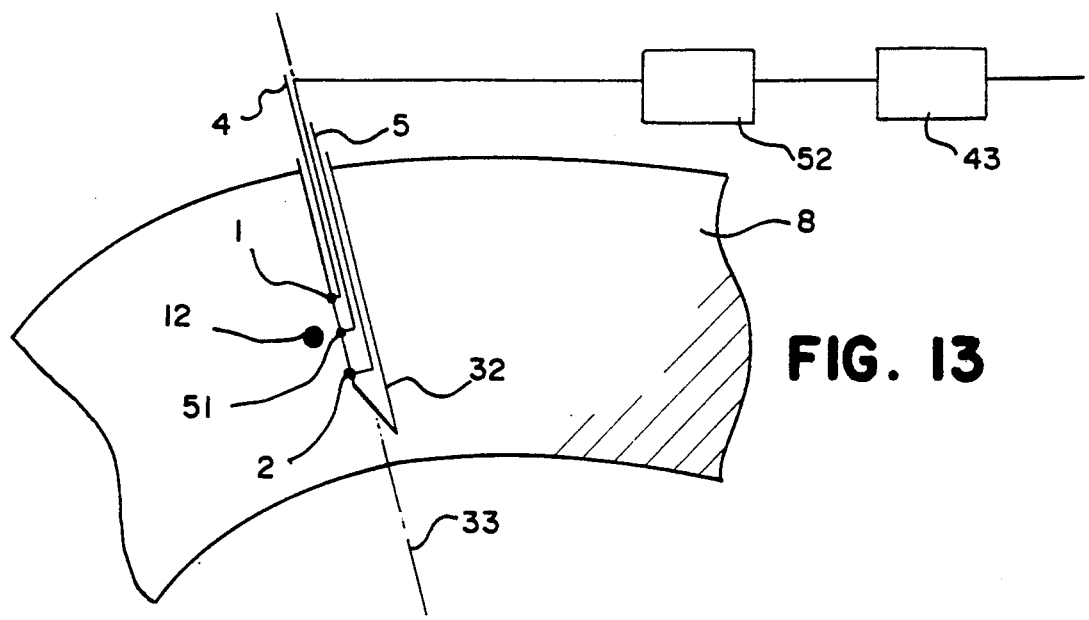
FIG. 13 shows, in section, an embodiment of the needle-probe given by way of example, with the arrangement of the electrodes, of the active portion of the means of destruction located on the needle-probe and of the generator which is associated therewith.

FIG. 13 shows the localization, on the needle (32) for example, of the active portion (51) of the means of destruction of the seat of activation (12) of the ventricular tachycardia.

Figure 11:
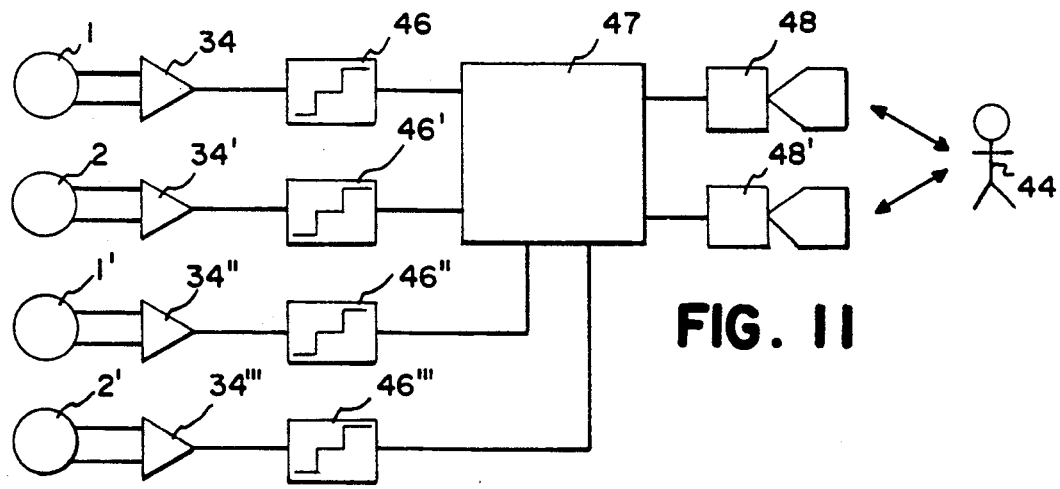
FIG. 11 shows the block diagram of the programmed version of the device.

In a second version of the device shown in FIG. 11, the electronic circuits are produced using programmed logic technology, carrying out functions similar to the wired version and comprising sensors (1), (2) and (1'), (2') connected to amplifiers (34), (34') and (34"), (34'''), followed by analogue-to-digital converters equipped with sampling/blocking units (46), (46') and (46"), (46'''), and a programmed processor (47) which carries out the acquisitions, filters and recognizes the signals, compares them and indicates to the operator (44) via the interfaces (48) and (48') the procedure to be followed in order to reach the emergence point. The processor (47) also carries out, where appropriate, the elimination of the stimulatory impulse in the processing of the signal. The four conversion systems (46), (46'), (46") and (46'''') may be replaced by four sampling/blocking units, followed by an analogue multiplexer, followed by a single analogue-to-digital converter.

I claim:

1. An apparatus for localizing an emergence point of a ventricular tachycardia in a heart, comprising:
   a probe including at least two sensors for contacting surface portions of the heart and defining a substantially rectilinear axis;
   electronic monitoring means for receiving electrical signals from the sensors, and for processing the electrical signals received from the sensors to determine a sense relative to the rectilinear axis and a direction of the emergence point, including means for measuring a phase shift between the electrical signals received from the sensors; and
   display means for receiving the processed electrical signals from the monitoring means, and for displaying the received, processed electrical signals to an operator of the apparatus;
   wherein the processed electrical signals displayed by the display means indicate the sense and the direction of the emergence point relative to propagation of a myocardial depolarization.

2. The apparatus of claim 1 wherein the phase shift measuring means includes means for making plural phase determinations, and means for indicating the direction of the emergence point responsive to said plural phase determinations.

3. The apparatus of claim 2 wherein the means for making plural phase determinations operates responsive to rotations of the probe about an axis perpendicular to the surface of the heart.

4. The apparatus of claim 3 having means for measuring a maximum phase shift between the signals received from the sensors, for indicating when the emergence point lies in the direction of the rectilinear axis.

5. The apparatus of claim 3 having means for measuring a phase shift between the signals received from the sensors which approaches zero, for indicating when the emergence point lies in a direction perpendicular to the rectilinear axis.

6. The apparatus of claim 3 having means for localizing the emergence point responsive to successive movements of the probe.

7. The apparatus of claim 6 wherein the localizing means includes means for measuring a zero phase shift in all directions.

8. The apparatus of claim 6 wherein the sensors are separated by less than 50 millimeters.

9. The apparatus of claim 1 wherein the probe has two pairs of sensors defining two axes on the probe.

10. The apparatus of claim 9 having means for electrically combining the electrical signals from the sensors in said monitoring means to define an azimuth indicating the sense and the direction of the emergence point.

11. The apparatus of claim 10 wherein the axes are substantially perpendicular to each other.

12. The apparatus of claim 11 wherein the paired sensors produce paired, phase-shifted signals, and wherein the monitoring means includes means for developing a vector indicating the sense and the direction of the emergence point responsive to a paired, phase-shifted signals of the sensors.

13. The apparatus of claim 1 wherein the probe further includes a needle for progressive introduction into the myocardium, for localizing the seat of activation of the ventricular tachycardia.

14. The apparatus of claim 13 wherein the probe includes a means for destroying the emergency point.

15. The apparatus of claim 1 wherein the electronic monitoring means comprises a plurality of amplifiers electrically connected to the sensors, a corresponding plurality of filters electrically connected to the amplifiers for selecting a desired frequency component of the electrical signals received from the sensors, and a corresponding plurality of hysteresis comparators electrically connected to the filters for producing logic signals for application to the display means.

16. The apparatus of claim 15 which further comprises a logic phase detector for receiving said logic signals from the hysteresis comparators and for producing a signal characteristic of a phase shift between the electrical signals provided by the sensors.

17. The apparatus of claim 16 which includes means for isolating the apparatus from external leakage currents within specified limits.

18. The apparatus of claim 17 which includes a limiter coupled with the amplifiers for protecting the amplifiers from voltage surges which are produced by other equipment used by the operator.

19. The apparatus of claim 17 which includes an analog switch coupled with the amplifiers for eliminating signals originating from a cardiac stimulator through the myocardium.

20. The apparatus of claim 19 having means for controlling the analog switch responsive to electrical impulses received from the stimulator.

21. The apparatus of claim 1 wherein the display means comprises an interface between the apparatus and the operator, for employing a physiological sense of the operator.

22. The apparatus of claim 1 wherein the electronic monitoring means includes a plurality of amplifiers for receiving the electrical signals from the sensors, sampling means for receiving amplified signals from the amplifiers, analog-to-analog conversion means coupled with the sampling means, and a computer coupled with the analog-to-digital conversion means and the display means.

23. A method for localizing an emergence point of a ventricular tachycardia in a heart, comprising the steps of:
   contacting surface portions of the heart with a probe including at least two sensors defining a substantially rectilinear axis;
   monitoring electrical signals received from the sensors, and processing the monitored electrical signals to determine a sense relative to the rectilinear axis and a direction of the emergence point, including measuring a phase shift between the electrical signals received from the sensors; and
   displaying the processed electrical signals to an operator, indicating the sense and the direction of the emergence point relative to propagation of a myocardial depolarization.

24. The method of claim 23 which further includes making plural phase determinations, wherein the direction is indicated responsive to said plural phase determinations.

25. The method of claim 24 wherein the plural phase determinations are made by rotating the probe about an axis perpendicular to the surface of the heart.

26. The method of claim 25 which further includes successively moving the probe until the emergence point is localized.

27. The method of claim 26 wherein the emergence point is localized when a zero phase shift is measured in all directions.

28. The method of claim 26 which further includes defining an azimuth indicating the sense and direction of the emergence point by electrically combining signals received from the sensors.

29. The method of claim 26 which further includes progressively introducing a needle associated with the probe into the myocardium to localize the seat of activation of the ventricular tachycardia.

30. The method of claim 29 which further includes destroying the emergence point.

31. The method of claim 26 which further includes eliminating signals originating from a cardiac stimulator through the myocardium.

32. The method of claim 31 wherein the cardiac stimulator signals are eliminated responsive to electrical impulses received from the stimulator.

33. The method of claim 26 which further includes interfacing with the operator, for employing a physiological sense of the operator.

34. The method of claim 25 which further includes measuring a maximum phase shift between the signals received from the sensors, indicating when the emergence point lies in the direction of the rectilinear axis.

35. The method of claim 25 which further includes measuring a phase shift between the signals received from the sensors which approaches zero, indicating when the emergence point lies in a direction perpendicular to the rectilinear axis.

* * * * *